US00PP24823P2

(12) United States Plant Patent
Smith

(10) Patent No.: US PP24,823 P2
(45) Date of Patent: Aug. 26, 2014

(54) ***CHRYSANTHEMUM* PLANT NAMED 'CIFZ0008'**

(50) Latin Name: *Chrysanthemum×morifolium*
Varietal Denomination: CIFZ0008

(71) Applicant: Syngenta Crop Protection AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 152 days.

(21) Appl. No.: 13/573,649

(22) Filed: Oct. 1, 2012

(51) Int. Cl.
*A01H 5/00* (2006.01)

(52) U.S. Cl.
USPC ..... Plt./287

(58) Field of Classification Search
USPC ..... Plt./287
See application file for complete search history.

*Primary Examiner* — Wendy C Haas
(74) *Attorney, Agent, or Firm* — Joshua L. Price

(57) ABSTRACT

A new *Chrysanthemum* plant named 'CIFZ0008' particularly distinguished by the greyed-purple ray floret color, medium to large sized decorative inflorescences, medium sized round shaped plant habit and a natural season response of late September to early October.

1 Drawing Sheet

Latin name of the genus and species of the plant claimed: *Chrysanthemum×morifolium.*

Varietal denomination: 'CIFZ0008'.

BACKGROUND OF THE NEW PLANT

The present invention comprises a new *Chrysanthemum*, botanically known as *Chrysanthemum×morifolium*, and hereinafter referred to by the variety name 'CIFZ0008'.

'CIFZ0008' is a product of a planned breeding program. The new cultivar has greyed-purple ray floret color, medium to large sized decorative inflorescences, medium sized round shaped plant habit and a natural season response of late September to early October.

'CIDZ0008' originates as a natural whole plant mutation of 'Sywan Pur', U.S. Plant Pat. No. 22,784. 'CIFZ0008' was discovered and selected by the inventor as a single flowering plant within a large population of the parent cultivar, grown massed in pots outdoors in a controlled breeding program in Alva, Fla. in November 2009. The parent cultivar 'Sywan Pur' has purple ray floret color with a little smaller plant size.

The first act of asexual reproduction of 'CIFZ0008' was accomplished when vegetative cuttings were propagated from the initial selection in January 2010 in a greenhouse in Alva, Fla.

BRIEF SUMMARY OF INVENTION

Horticultural examination of plants grown from cuttings of the plant initiated in January 2010, and continuing thereafter, has demonstrated that the combination of characteristics as herein disclosed for 'CIFZ0008' are firmly fixed and are retained through successive generations of asexual reproduction.

'CIFZ0008' has not been observed under all possible environmental conditions. The phenotype may vary significantly with variations in environment such as temperature, light intensity, and day length.

A Plant Breeder's Right for this cultivar was applied for in Canada on Feb. 24, 2012 (12-7527). 'CIFZ0008' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0008' with colors being as true as possible with an illustration of this type.

Figure 1:
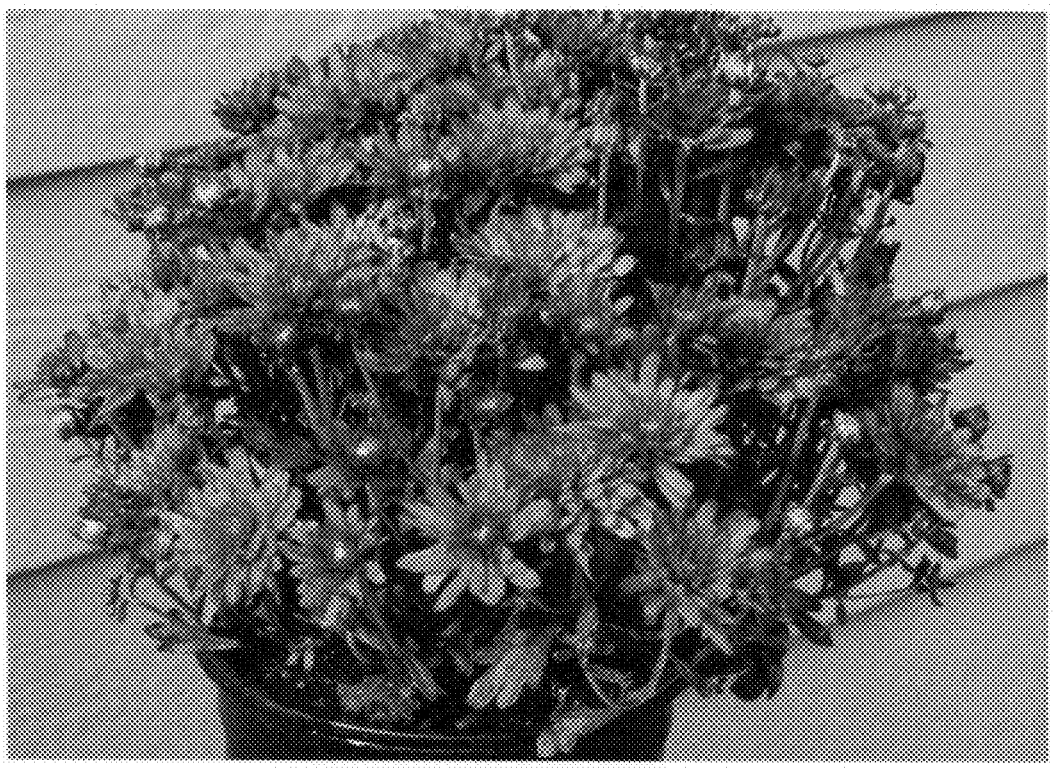
Figure 2:
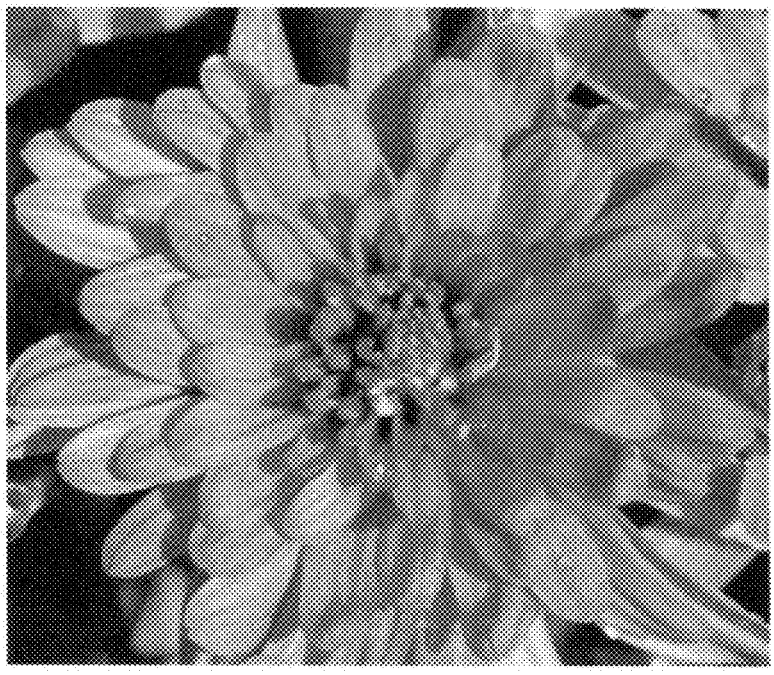

The photographic drawings show in FIG. 1 a flowering plant of the new variety and in FIG. 2 a close-up of the inflorescences.

DETAILED BOTANICAL DESCRIPTION

The plant descriptions, measurements and aforementioned photographs were taken in Gilroy, Calif. in early August 2012 outdoors. These plants were approximately 12-14 weeks of age, grown in 1 gallon pots in full-sun outdoor trials.

Color references are made to The Royal Horticultural Society Colour Chart (R.H.S.) 2001.

TABLE 1

DIFFERENCES BETWEEN THE NEW VARIETY 'CIFZ0008' AND A MOST SIMILAR VARIETY

| | 'CIFZ0008' | 'Foxy Yomarjorie' (U.S. Plant Pat. No. 15,829) |
|---|---|---|
| Plant habit type: | Bit fuller/more compact | Less full/less compact |
| Blackcloth flowering response time: | Half a week faster | Half a week slower |
| Inflorescence size: | Larger | Smaller |
| Disc floret quantity: | Fewer | More |

Plant:

*Form, growth and habit.*—Herbaceous garden-type, stems upright and outwardly spreading, freely branching, strong and moderately vigorous growth habit.

*Plant height.*—15-17.0 cm.

*Plant height (inflorescence included).*—20-23.0 cm.

*Plant width.*—About 35.0 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137A.

*Immature, leaf color, lower surface.*—RHS 137C to RHS 137D.

*Mature, leaf color, upper surface.*—Closest to RHS 137A.

*Mature, leaf color, lower surface.*—RHS 137C to RHS 137D.

*Length.*—3-3.5 cm.

*Width.*—2.6-2.9 cm.

*Shape.*—Ovate.

*Base shape.*—Attenuate.

*Apex shape.*—Mucronulate.

*Margin.*—Slightly palmately lobed; slightly serrulate.

*Texture, upper surface.*—Bifid T-shaped hairs.

*Textures, lower surface.*—Bifid T-shaped hairs.

*Color of veins, upper surface.*—RHS 137D.

*Color of veins, lower surface.*—RHS 137D.

*Pattern of veining.*—Palmate.

*Petiole color.*—RHS 137D.

*Length.*—0.7-0.9 cm.

*Diameter.*—0.2 cm.

*Texture.*—Bifid T-shaped hairs.

Stem:

*Quantity of main branches per plant.*—6-8.

*Color of stem.*—Closest to RHS 146A vbut appears lighter due to hairs.

*Length of stem.*—10-12.0 cm.

*Diameter.*—0.4-0.5 cm.

*Length of internodes.*—0.5-0.75 cm.

*Texture.*—Bifid T-shaped hairs.

*Color of peduncle.*—Closest to RHS 146A.

*Length of peduncle.*—5.5-9.0 cm.

*Peduncle diameter.*—0.2 cm.

*Texture.*—Bifid T-shaped hairs.

Inflorescence:

*Type.*—Solitary decorative inflorescences borne terminally above foliage, ray florets arranged acropetally on a capitulum.

*Quantity of short days to flowering (response time).*—45-49, but can be shorter in warmer temperatures.

*Natural season flowering.*—Late September to early October.

*Quantity of inflorescences per plant.*—75-85 with an additional 60-75 buds in various stages.

*Lastingness of individual blooms on the plant.*—About 6 weeks from first color.

*Fragrance.*—Slightly spicy.

Bud (just when opening/showing color):

*Color.*—Closest to RHS 187B.

*Length.*—1.1-1.5 cm.

*Width.*—1.1-1.3.

*Shape.*—Oblate.

Immature inflorescence:

*Diameter.*—3.5-4.0 cm.

*Color of ray florets, upper surface.*—Between RHS 187B and RHS 187C.

*Color of ray florets, lower surface.*—Closest to RHS N186D.

Mature inflorescence:

*Diameter.*—5.6-6.2 cm.

*Depth.*—1.5-1.8 cm.

*Total diameter of disc.*—0.1-0.2 cm.

*Receptacle color.*—RHS N144D.

*Receptacle height.*—0.6 cm.

*Receptacle diameter.*—0.5-0.6 cm.

Ray florets:

*Quantity of florets.*—About 150 in many whorls.

*Color of florets, upper surface.*—Closest to RHS 187C, many with slightly lighter color and longitudinal striations where the floret is losing the color.

*Color of florets, lower surface.*—RHS N186D with lighter patches.

*Length.*—2.7-3.0 cm.

*Width.*—0.5-0.6 cm.

*Shape.*—Oblong; and slightly twisted when very mature.

*Apex shape.*—Irregularly emarginated some almost praemorse.

*Margin.*—Entire.

*Texture, upper surface.*—Papillose.

*Textures, lower surface.*—Papillose.

Disc florets:

*Quantity of florets.*—0-2.

*Color of florets.*—RHS 1C with a RHS 9B apex.

*Length.*—0.5 cm.

*Width.*—0.1 cm.

*Shape.*—Tubular, elongated.

*Apex shape.*—Acute, 5 pointed.

*Texture, inner surface.*—Glabrous.

*Texture, outer surface.*—Glabrous.

Phyllaries:

*Quantity.*—About 100 including all bracts.

*Color, upper surface.*—RHS 137D.

*Color, lower surface.*—RHS 137B.

*Length.*—0.6-0.8 cm.

*Width.*—0.2 cm.

*Shape.*—Lanceolate.

*Apex shape.*—Acute.

*Based.*—Fused.

*Margins.*—Entire.

*Texture, upper surface.*—Glabrous.

*Texture, lower surface.*—Bifid T-shaped hairs.

Reproductive organs:

*Gynoecium.*—

*Pistil.*—1, found on both types of florets.

*Length.*—0.3-0.4 cm.

*Style color.*—RHS 1C.

*Style length.*—0.3 cm.

*Stigma color.*—RHS 3B.

*Stigma shape.*—Bi-parted.

*Ovary color and size.*—Not determinable at the time.

*Androecium.*—
*Stamens.*—4, found on only on the disc florets.
*Color of filaments.*—RHS 1C.
*Length filaments.*—0.185 cm.
*Anther color.*—RHS 3A.
*Anther length.*—0.15 cm.
*Anther shape.*—Oblong.
*Color of pollen.*—RHS 7C.
*Pollen amount.*—Very sparse.
*Fertility/seed set.*—Has not been determined to date.
*Disease/pest resistance.*—Has not been determined to date.

What is claimed is:

1. A new and distinct variety of *Chrysanthemum* plant named 'CIFZ0008' substantially as illustrated and described herein.

* * * * *